United States Patent [19]

Barter et al.

[11] 4,394,328

[45] Jul. 19, 1983

[54] PRODUCTION OF PEROXYDICARBONATES

[75] Inventors: James A. Barter, Akron; David E. Kellar, Barberton, both of Ohio

[73] Assignee: PPG Industries, Inc., Pittsburgh, Pa.

[21] Appl. No.: 134,370

[22] Filed: Mar. 27, 1980

Related U.S. Application Data

[63] Continuation-in-part of Ser. No. 920,886, Jun. 30, 1978, abandoned.

[51] Int. Cl.³ .............................................. C07C 68/02
[52] U.S. Cl. ................................................. 260/463
[58] Field of Search ........................................ 260/463

[56] References Cited

U.S. PATENT DOCUMENTS

| | | | |
|---|---|---|---|
| 2,370,588 | 2/1945 | Strain | 260/463 |
| 2,464,062 | 3/1949 | Strain | 260/95 R |
| 3,377,373 | 4/1968 | Lederer et al. | 260/463 |
| 3,429,910 | 2/1969 | Lederer et al. | 260/463 |
| 3,720,700 | 3/1973 | Norback | 260/463 |
| 3,821,273 | 6/1974 | D'Angelo | 260/463 |
| 4,137,252 | 1/1979 | Komai et al. | 260/463 |

FOREIGN PATENT DOCUMENTS

| | | | |
|---|---|---|---|
| 1443840 | 10/1968 | Fed. Rep. of Germany | 260/463 |
| 2727027 | 12/1977 | Fed. Rep. of Germany | 260/463 |
| 1267949 | 3/1972 | United Kingdom | 260/463 |

*Primary Examiner*—Anton H. Sutto
*Attorney, Agent, or Firm*—Edward J. Whitfield

[57] ABSTRACT

A process for preparing peroxydicarbonate is disclosed wherein a mixture of chloroformate and dilute aqueous hydrogen peroxide is reacted with a dilute aqueous alkali metal hydroxide solution.

7 Claims, No Drawings

PRODUCTION OF PEROXYDICARBONATES

CROSS-REFERENCE TO RELATED APPLICATION

This application is a continuation-in-part of application Ser. No. 920,886, filed June 30, 1978, now abandoned.

BACKGROUND OF THE INVENTION

Peroxydicarbonates of the formula R—OCO—OO—OCO—R, wherein R is an organic radical derived from monohydric alcohols of the type ROH, are widely used as initiators in the polymerization of unsaturated monomers as described, for example, in U.S. Pat. No. 2,464,062.

The peroxydicarbonates are typically prepared by the so-called "peroxide slurry method" wherein a chloroformate of the formula R—OCO—Cl (wherein R is as above defined) is reacted with a concentrated aqueous slurry of sodium peroxide as described, for example, in U.S. Pat. No. 2,370,588.

It has been found, however, that during the addition of the sodium peroxide slurry to the reaction mixture, the reaction product tends to hydrolyze to form the corresponding alcohol resulting in an impure product having a reduced peroxydicarbonate assay. In addition, hydrolysis of the reaction product reduces the net yield of peroxydicarbonate.

Since the lower molecular weight alcohols, for example, ethanol, isopropanol, n-propanol, t-butanol, sec-butanol, and the like are relatively water soluble, such lower molecular weight alcoholic impurities can be readily removed from the peroxydicarbonate by washing with water. However, since the water solubility of alcohols generally decreases with increasing molecular weight, the higher molecular weight alcoholic impurities such as, for example, 2-ethylhexanol, are not readily removed from the peroxydicarbonate by typical product purification means, e.g., water washing.

Regardless of the ease of removal of the alcoholic impurity formed by hydrolysis of the reaction product upon addition of the sodium peroxide slurry, the yield of peroxydicarbonate is reduced in proportion to the extent of hydrolysis.

Published German Patent application No. 1,443,840 discloses adding sodium hydroxide to a colloidal dispersion of hydrogen peroxide and chloroformate, which entails the use of costly, complex equipment. Moreover, the process described in said German application requires the addition of a perhalogenated solvent before, during or at the completion of the reaction, with the consequence that only dilute solvent solutions of peroxydicarbonate are obtained. Although the German application states that peroxydicarbonate can be recovered from the solvent solution by distillation, this requires an additional costly and time consuming processing step which is potentially hazardous.

SUMMARY OF THE INVENTION

High purity peroxydicarbonate is produced in high yield by reacting a mixture containing chloroformate and dilute aqueous hydrogen peroxide with a dilute aqueous alkali metal hydroxide solution. The process of the invention is conducted batchwise, and requires only simple agitation or stirring sufficient to adequately mix the reactants to bring them into intimate contact thus avoiding the necessity of having to form a colloidal dispersion of the hydrogen peroxide and chloroformate.

DESCRIPTION OF THE INVENTION

In accordance with this invention, a peroxydicarbonate of the formula R—OCO—OO—OCO—R is prepared by reacting a mixture containing dilute aqueous hydrogen peroxide and a chloroformate of the formula R—OCO—Cl, with a dilute aqueous alkali metal hydroxide solution.

The invention is particularly applicable to producing di-n-propyl peroxydicarbonate (NPP), diisopropyl peroxydicarbonate (IPP), di-sec-butyl peroxydicarbonate (SBP), and di-(2-ethylhexyl) peroxydicarbonate (EHP), although in its broadest aspects, the invention contemplates the production of other peroxydicarbonates in addition to the preferred NPP, IPP, SBP and EHP.

Thus, although in the above formulae R preferably represents n-propyl, isopropyl, sec-butyl, and 2-ethylhexyl, R may represent other linear or branched, substituted or unsubstituted alkyl or cycloalkyl radicals derived from a monohydric alcohol and containing up to about 18 carbon atoms. Other organic radicals of which R is representative include, for example, ethyl, butyl, n-butyl, isobutyl, t-butyl, hexyl, cyclohexyl, benzyl, 2-phenoxy ethyl, cetyl, allyl, tetradecyl, amyl, lauryl, and the like.

The chloroformate aqueous hydrogen peroxide mixture contains from about 10 percent to 35 percent by weight and preferably from about 14 percent to about 30 percent by weight hydrogen peroxide based on the weight of water, with sufficient hydrogen peroxide being present to provide at least about a 4 percent stoichiometric excess and preferably an 8 percent to 12 percent stoichiometric excess of hydrogen peroxide based on the quantity of chloroformate.

The chloroformate aqueous hydrogen peroxide mixture may also contain from about 5 percent to about 15 percent, preferably about 10 percent by weight, based on the weight of chloroformate, of a lower alcohol or mixture of lower alcohols, such as, for example, methanol, ethanol, isopropanol, n-propanol, or the like. The inclusion of a lower alcohol has been found to enable better reaction temperature control.

In order to produce high purity, i.e., 98 percent or higher, peroxydicarbonate, the chloroformate starting material, should, of course be as pure as possible. Chloroformate having an assay of at least 99 percent is preferred for use in accordance with the invention.

The aqueous alkali metal hydroxide solution contains from about 20 percent to 40 percent by weight, preferably from about 25 percent to 35 percent by weight alkali metal hydroxide, sufficient of said solution being used for reaction with the chloroformate/hydrogen peroxide mixture to provide at least about a 1 percent and preferably from about 2 to 10 percent stoichiometric excess of alkali metal hydroxide based on the quantity of chloroformate.

The alkali metal hydroxide may be sodium hydroxide or potassium hydroxide as each has been found to give substantially equivalent results.

The reaction between the hydrogen peroxide/chloroformate mixture and the alkali metal hydroxide solution is conducted with continuous stirring at a temperature of from about −10° C. to not more than about 30° C., preferably not more than about 15° C.

The alkali metal hydroxide solution is added, with continuous stirring, to the hydrogen peroxide/chloroformate mixture incrementally over a period of about 10 minutes to one hour, usually not more than 30 minutes. Following the addition of the alkali metal hydroxide solution, the mixture is usually stirred for an additional period typically not more than about 30 minutes and usually not more than about 10 to 15 minutes to assure substantially complete conversion of chloroformate to peroxydicarbonate.

At the completion of the reaction, liquid or solid peroxydicarbonate is recovered by any suitable, conventional means. In the case of liquid peroxydicarbonate, the reaction mixture readily phase separates and the organic or peroxydicarbonate phase is drawn-off, washed with cold water to remove water soluble impurities and dried by, for example, contact with an inert drying agent such as, magnesium sulfate or sodium sulfate. A solid peroxydicarbonate may be recovered by sedimentation or centrifugation followed by washing with cold water and drying.

Peroxydicarbonate assaying in excess of 98 percent with substantially quantitative conversion of chloroformate can routinely be obtained by the practice of this invention.

Although the invention has been described with particular reference to a preferred embodiment, it is evident that variations may be made therein without departing from the spirit and scope thereof. For example, it has been found that satisfactory results are obtained by simultaneously adding a dilute aqueous hydrogen peroxide solution along with a dilute aqueous alkali metal hydroxide solution to the chloroformate. The respective strengths of said solutions and the stoichiometric excesses of hydrogen peroxide and alkali metal hydroxide are the same as described hereinabove with respect to the preferred manner of practicing the invention, i.e., by adding the alkali metal hydroxide solution to the hydrogen peroxide/chloroformate mixture.

The process of this invention enables the production of higher yields of higher purity peroxydicarbonate in a shorter reaction time with better reaction temperature control than the heretofore used peroxide slurry method. The process of this invention also avoids the disadvantages attendant on forming and handling colloidal dispersions or emulsions of hydrogen peroxide and chloroformate.

The invention is further illustrated by the following examples.

EXAMPLE 1

The reactor used consisted of a 500 milliliter capacity round bottom, three-neck flask. The flask was fitted with a pH electrode, a type "J" thermocouple, and a stirring rod having a TEFLON ® paddle powered by a variable speed mixer. The temperature of the reactor was controlled by pumping ice water through a spray ring positioned around the reactor.

96.3 grams (0.5 mole) 2-ethylhexyl chloroformate, 65.1 grams of 14.1 weight percent aqueous hydrogen peroxide solution (0.27 mole $H_2O_2$), and 9.63 grams of isopropanol were added to the reactor. 81 grams of 25.7 weight percent aqueous sodium hydroxide solution (0.52 mole NaOH) were added to the reactor over a 25 minute period. After completion of the sodium hydroxide addition, the mixture was permitted to react for an additional 30 minutes. Throughout the sodium hydroxide solution addition period and reaction period, the reactor contents were continuously stirred and maintained at a temperature of 15° C.

At the completion of the reaction, stirring was discontinued and the reaction mixture was permitted to phase separate. The organic phase was withdrawn, washed with cold water, dried with sodium sulphate, and submitted for analysis. Di(2-ethylhexyl) peroxydicarbonate product assaying at 99.3 percent was obtained.

EXAMPLE 2

136.5 grams (1 mole) of sec-butyl chloroformate, 62 grams of 30.5 weight percent aqueous hydrogen peroxide solution (0.56 mole $H_2O_2$), and 13.65 grams isopropanol were added to the reactor described in Example 1. 109 grams of 40.4 weight percent aqueous sodium hydroxide solution (1.1 mole NaOH) were added to the reactor over a 30 minute period and the reaction mixture was permitted to react an additional 30 minutes. The reactor contents were continuously stirred and maintained at a temperature of 15° C. throughout the addition of the sodium hydroxide solution and the reaction period.

At the completion of the reaction, stirring was discontinued, the reaction mixture was permitted to phase separate, the organic phase was withdrawn, washed with cold water, dried with sodium sulphate, and submitted for analysis. Di-sec-butyl peroxydicarbonate assaying at 99.2 percent was obtained.

EXAMPLE 3

122.5 grams (1 mole) of isopropyl chloroformate and 91.3 grams of 20.5 weight percent aqueous hydrogen peroxide solution (0.55 moles $H_2O_2$) were added to the reactor described in Example 1. 130 grams of 32.3 weight percent aqueous sodium hydroxide solution (1.05 moles NaOH) were added to the reactor over a 34 minute period and the reaction mixture was permitted to react an additional 30 minutes. The contents of the reactor was continuously stirred and maintained at a temperature of 15° C. throughout the addition of the sodium hydroxide solution and the reaction period.

At the completion of the reaction, stirring was discontinued, the reaction product was phase separated, the organic phase was withdrawn, washed with cold water, dried with sodium sulphate, and submitted for analysis. Diisopropyl peroxydicarbonate assaying at 99.0 percent was obtained.

EXAMPLE 4

The procedure of Example 3 was followed except that n-propyl chloroformate was used in place of isopropyl chloroformate. Di-n-propyl peroxydicarbonate assaying at 99.4 percent was obtained.

EXAMPLE 5

96.3 grams of 2-ethylhexyl chloroformate, 9.63 grams of isopropanol, and 25 grams of water were added to the reactor described in Example 1. 40.94 grams of 50.8 percent aqueous sodium hydroxide solution was diluted with 25 grams of water. 18.18 grams of 50.5 percent aqueous hydrogen peroxide solution was diluted with 40 grams of water. Each solution had a volume of 53 milliliters. Each solution was added separately but simultaneously to the reactor via a dual-head Master Flex pump over a period of about 33 minutes. After completion of addition of the sodium hydroxide and hydrogen perioxide solutions, the mixture was permitted to react for an additional 30 minutes. Throughout the solution addition period and reaction period, the reactor contents were continuously stirred and maintained at a temperature of 15° C.

At the completion of the reaction, stirring was discontinued, the reaction mixture was permitted to phase separate, the organic phase was withdrawn, washed with cold water, dried with sodium sulphate, and submitted for analysis. Di(2-ethylhexyl) peroxydicarbonate assaying at 99.1 percent was obtained.

Although the invention has been described with specific references and specific details of embodiments thereof, it is to be understood that it is not intended to be so limited since changes and alterations therein may be made by those skilled in the art which are within the full intended scope of this invention as defined by the appended claims.

We claim:

1. In a process for preparing peroxydicarbonate represented by the formula R—OCO—OO—OCO—R wherein R is an alkyl or cycloalkyl radical derived from a monohydric alcohol and containing up to 18 carbon atoms by reacting, at a temperature of from −10° C. to 30° C., a chloroformate of the formula R—OCO—Cl, wherein R is as defined above, with hydrogen peroxide and alkali metal hydroxide and recovering undiluted peroxydicarbonate from the reaction mixture, wherein the improvement resides in adding aqueous alkali metal hydroxide solution, containing from 20 percent to 40 percent by weight alkali metal hydroxide, to a continuously stirred batch of an aqueous unemulsified, non-colloidal mixture consisting essentially of chloroformate and hydrogen peroxide the mixture containing from 4 to 12 percent stoichiometric excess of hydrogen peroxide based on the quantity of chloroformate and having a hydrogen peroxide content of from about 10 percent to about 35 percent by weight based on the quantity of water in the mixture, sufficient alkali metal hydroxide solution being added to the mixture so as to provide from 1 to 10 percent stoichiometric excess of alkali metal hydroxide based on the quantity of chloroformate in the mixture.

2. The improvement of claim 1 wherein the chloroformate is selected from n-propyl chloroformate, isopropyl chloroformate, sec-butyl chloroformate, and 2-ethylhexyl chloroformate.

3. The improvement of claim 2 wherein the chloroformate is selected from sec-butyl chloroformate and 2-ethylhexyl chloroformate and the chloroformate/hydrogen peroxide mixture contains from about 5 to 15 percent by weight of a lower alcohol based on the weight of chloroformate.

4. The improvement of claim 3 wherein the lower alcohol is selected from methanol, ethanol, n-propanol, isopropanol, or t-butanol.

5. The improvement of claim 1 wherein the alkali metal hydroxide is selected from sodium hydroxide or potassium hydroxide.

6. The improvement of claim 1 wherein the alkali metal hydroxide solution is added to the chloroformate/hydrogen peroxide mixture over a period of about 10 minutes to one hour.

7. The improvement of claim 1 wherein sufficient hydrogen peroxide and alkali metal hydroxide are used so as to respectively provide 4 to 12 percent and 2 to 10 percent stoichiometric excesses based on the quantity of chloroformate.

* * * * *